(12) United States Patent
Kaib

(10) Patent No.: US 9,272,131 B2
(45) Date of Patent: Mar. 1, 2016

(54) FLEXIBLE AND/OR TAPERED THERAPY ELECTRODE

(71) Applicant: ZOLL MEDICAL CORPORATION, Chelmsford, MA (US)

(72) Inventor: Thomas E. Kaib, North Huntingdon, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 14/523,234

(22) Filed: Oct. 24, 2014

(65) Prior Publication Data

US 2015/0045870 A1 Feb. 12, 2015

Related U.S. Application Data

(63) Continuation of application No. 13/784,074, filed on Mar. 4, 2013, now Pat. No. 8,880,196.

(51) Int. Cl.
*A61N 1/00* (2006.01)
*A61N 1/04* (2006.01)
*A61N 1/39* (2006.01)

(52) U.S. Cl.
CPC .............. *A61N 1/046* (2013.01); *A61N 1/0484* (2013.01); *A61N 1/0496* (2013.01); *A61N 1/3987* (2013.01)

(58) Field of Classification Search
USPC ........................................... 607/149, 2; 2/114
See application file for complete search history.

(56) References Cited

U.S. PATENT DOCUMENTS

| | | | |
|---|---|---|---|
| 3,467,863 A | 9/1969 | Karsh | |
| 4,094,310 A | 6/1978 | McEachern et al. | |
| 4,464,412 A | 8/1984 | Washburn | |
| 4,632,122 A | 12/1986 | Johansson et al. | |
| 4,928,690 A | 5/1990 | Heilman et al. | |
| 4,978,926 A | 12/1990 | Zerod et al. | |
| 5,062,834 A | 11/1991 | Gross et al. | |
| 5,078,134 A | 1/1992 | Heilman et al. | |
| 5,348,008 A | 9/1994 | Bornn et al. | |
| 5,365,932 A | 11/1994 | Greenhut | |

(Continued)

FOREIGN PATENT DOCUMENTS

| | | |
|---|---|---|
| EP | 00339471 A2 | 11/1989 |
| EP | 0295497 B1 | 9/1993 |

(Continued)

OTHER PUBLICATIONS

DeBock, et al., "Captopril treatment of chronic heart failure in the very old," J. Gerontol. (1994) 49: M148-M152.

(Continued)

*Primary Examiner* — Nicole F Lavert
(74) *Attorney, Agent, or Firm* — Lando & Anastasi, LLP

(57) ABSTRACT

An electrode assembly includes a first surface to be placed adjacent a person's skin and a second surface including a plurality of reservoirs of conductive gel. The plurality of reservoirs of conductive gel are disposed on sections of the electrode assembly that are at least partially physically separated and may move at least partially independently of one another to conform to contours of a body of a patient. The electrode assembly is configured to dispense an amount of the electrically conductive gel onto the first surface in response to an activation signal and to provide for a defibrillating shock to be applied to the patient through the amount of the electrically conductive gel.

19 Claims, 13 Drawing Sheets

(56) References Cited

U.S. PATENT DOCUMENTS

| | | |
|---|---|---|
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,065,154 A | 5/2000 | Hulings et al. |
| 6,097,987 A | 8/2000 | Milani |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,908,437 B2 | 6/2005 | Bardy |
| 6,990,373 B2 | 1/2006 | Jayne et al. |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,488,293 B2 | 2/2009 | Marcovecchio et al. |
| 7,831,303 B2 | 11/2010 | Rueter et al. |
| 7,970,451 B2 | 6/2011 | Hassonjee et al. |
| 7,974,689 B2 | 7/2011 | Volpe et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,406,842 B2 | 3/2013 | Kaib et al. |
| 2003/0004547 A1 | 1/2003 | Owen et al. |
| 2003/0095648 A1 | 5/2003 | Kaib et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2005/0049515 A1 | 3/2005 | Misczynski et al. |
| 2005/0131465 A1 | 6/2005 | Freeman et al. |
| 2006/0036292 A1 | 2/2006 | Smith et al. |
| 2006/0085049 A1 | 4/2006 | Cory et al. |
| 2006/0270952 A1 | 11/2006 | Freeman et al. |
| 2007/0118056 A1 | 5/2007 | Wang et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2008/0000006 A1* | 1/2008 | Ochoa et al. ................ 2/114 |
| 2008/0004536 A1 | 1/2008 | Baxi et al. |
| 2008/0030656 A1 | 2/2008 | Watson et al. |
| 2008/0033495 A1 | 2/2008 | Kumar |
| 2008/0045815 A1 | 2/2008 | Derchak et al. |
| 2008/0058884 A1 | 3/2008 | Matos |
| 2008/0249591 A1 | 10/2008 | Gaw et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0234716 A1 | 9/2010 | Engel |
| 2010/0298899 A1 | 11/2010 | Donnelly et al. |
| 2011/0028822 A1 | 2/2011 | Beck |
| 2011/0288604 A1 | 11/2011 | Kaib et al. |
| 2011/0288605 A1 | 11/2011 | Kaib et al. |
| 2011/0312644 A1 | 12/2011 | Silverbrook et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0158075 A1 | 6/2012 | Kaib et al. |
| 2013/0144357 A1* | 6/2013 | Forward ................ 607/39 |
| 2014/0213875 A1 | 7/2014 | Freeman et al. |
| 2015/0217108 A1 | 8/2015 | Kaib et al. |

FOREIGN PATENT DOCUMENTS

| | | |
|---|---|---|
| EP | 0335356 B1 | 3/1996 |
| EP | 1455640 B1 | 1/2008 |
| EP | 1720446 B1 | 7/2010 |
| JP | 5115450 A | 5/1993 |
| WO | 0002484 A1 | 1/2000 |
| WO | 2004054656 A1 | 7/2004 |
| WO | 2008116822 A2 | 10/2008 |

OTHER PUBLICATIONS

Notification of Transmittal of the International Search Report and the Written Opinion of the International Searching Authority from corresponding PCT/US2014/01730 dated May 15, 2014.

O'Keeffe et al., "Reproducability and responsiveness of quality of life assessment and six minute walk test in elderly heart failure patients," Heart (1998) 80: 377-382.

* cited by examiner

FLEXIBLE AND/OR TAPERED THERAPY ELECTRODE

RELATED APPLICATIONS

This application claims the benefit under 35 U.S.C. §120 as a continuation of U.S. application Ser. No. 13/784,074 (now U.S. Pat. No. 8,880,196), titled "FLEXIBLE THERAPY ELECTRODE," filed on Mar. 4, 2013, which is herein incorporated by reference in its entirety.

BACKGROUND OF THE INVENTION

1. Field of the Invention

The present invention is directed to medical electrodes, and more particularly, to flexible medical electrodes that may be used with a wearable medical device, such as a defibrillator.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. These efforts are expensive and have a limited success rate, and cardiac arrest, among other conditions, continues to claim the lives of victims.

To protect against cardiac arrest and other cardiac health ailments, some at-risk patients may use a wearable defibrillator, such as the LifeVest® wearable cardioverter defibrillator available from ZOLL Medical Corporation of Chelmsford, Mass. To remain protected, the patient wears the device nearly continuously while going about their normal daily activities, while awake, and while asleep.

SUMMARY

In accordance with an aspect of the present invention, there is provided an electrode system. The electrode system comprises a substrate including a plurality of conductive gel reservoirs disposed on a first side thereof, a first of the plurality of conductive gel reservoirs disposed in a first segment of the substrate and a second of the plurality of the conductive gel reservoirs disposed in a second segment of the substrate, a fluid channel in fluid communication with a fluid source, the first of the plurality of conductive gel reservoirs, and the second of the plurality of the conductive gel reservoirs, and one of a slot or a gap defined in the substrate and extending from a region proximate the fluid channel and between the first of the plurality of conductive gel reservoirs and the second of the plurality of the conductive gel reservoirs to an edge of the substrate distal from the fluid channel. The one of the slot or the gap physically separates at least a portion of the first segment of the substrate from the second segment of the substrate.

In accordance with some embodiments, the electrode system further comprises an electrically conductive layer having a first surface disposed on a second side of the substrate and having a second surface configured to be disposed adjacent to a patient's skin.

In accordance with some embodiments, the plurality of conductive gel reservoirs and the fluid channel are included in a first impedance reduction system configured to dispense a first amount of a first electrically conductive gel onto the second surface of the electrically conductive layer in response to a first activation signal, and wherein the electrode system further includes a second impedance reduction system configured to dispense a second amount of a second electrically conductive gel onto the second surface of the electrically conductive layer in response to a second activation signal.

In accordance with some embodiments, the first impedance reduction system is similar in construction to the second impedance reduction system.

In accordance with some embodiments, the electrode system further comprises a garment wearable on a torso of a patient, the garment including a pocket formed from a layer of fabric and configured to receive the electrode system, wherein the electrode system is configured to dispense an amount of a conductive gel through the layer of fabric and into contact with the patient's skin.

In accordance with some embodiments, the electrode system further comprises an electrically conductive layer disposed on a second side of the substrate, the electrically conductive layer including a plurality of apertures configured to dispense the amount of the conductive gel.

In accordance with some embodiments, the electrode system further comprises an electrically conductive pathway included in the layer of fabric, the electrically conductive pathway configured to deliver electrical energy to the patient's skin through the amount of conductive gel dispensed from the electrode system.

In accordance with some embodiments, the layer of fabric is formed from an electrically conductive material.

In accordance with some embodiments, each of the substrate and the pocket are tapered to permit the electrode system to be received in the pocket in only a single orientation.

In accordance with some embodiments, the electrode system further comprises at least one ECG sensing electrode configured to monitor an ECG signal of a patient, the at least one ECG sensing electrode being disposed on a second side of the substrate and electrically insulated from portions of the electrode system configured to receive conductive gel.

In accordance with some embodiments, the electrode system further includes at least one additional sensor configured to monitor a physiological parameter of the patient other than an ECG signal of the patient.

In accordance with some embodiments, the at least one additional sensor is disposed on a third segment of the substrate, the third segment of the substrate at least partially physically separated by one of a slot or a gap defined in the substrate from portions of the substrate on which the plurality of conductive gel reservoirs are disposed.

In accordance with some embodiments, the substrate further comprises a plurality of additional segments positioned adjacent to one another and at least partially physically separated from one or another by slots or gaps defined in the substrate, each of the plurality of additional segments including a conductive gel reservoir disposed on first side thereof.

In accordance with some embodiments, the fluid pressure source is disposed on a third segment of the substrate, the third segment of the substrate being at least partially physically separated by one of a slot or a gap defined in the substrate from portions of the substrate on which the plurality of conductive gel reservoirs are disposed.

In accordance with some embodiments, the substrate is tapered from a first end to a second end, the taper of the substrate preventing insertion of the electrode system into a tapered pocket of a wearable medical device in an undesired direction.

In accordance with some embodiments, the electrode system further comprises a magnet disposed on a portion of the substrate and configured to apply a force to a magnet disposed on a pocket of a garment in which the electrode system can be inserted, the applied force providing an indication of proper orientation of the electrode system in the pocket.

In accordance with some embodiments, the electrode system further comprises a snap disposed on a portion of the substrate and configured to engage a corresponding snap disposed on a pocket of a garment in which the electrode system can be inserted, the engagement of the snap with the corresponding snap providing an indication of proper orientation of the electrode system in the pocket.

In accordance with some embodiments, the substrate comprises a fabric permeable to conductive gel which the electrode assembly is configured to dispense.

In accordance with some embodiments, the substrate is perforated.

In accordance with some embodiments, the electrode system includes an indicator disposed on an externally visible surface of the electrode system and configured to visually indicate whether the fluid source has been actuated.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
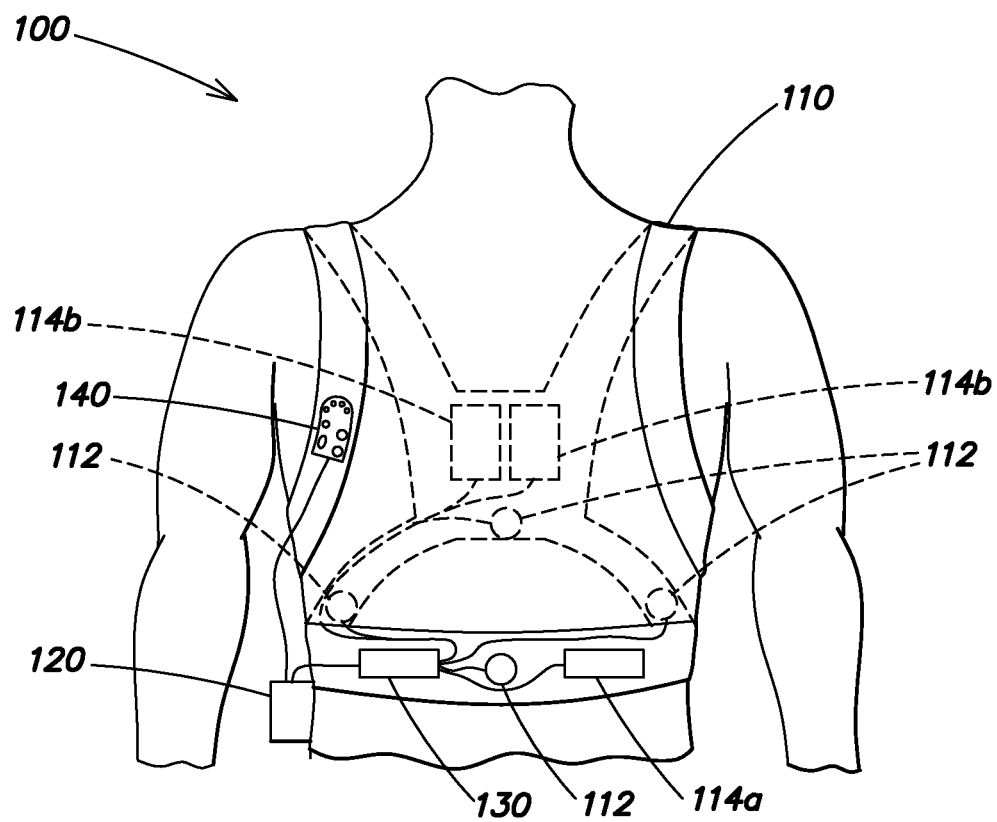
FIG. 1 illustrates a wearable medical device, such as a wearable defibrillator.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

FIG. 1 illustrates a wearable medical device, such as a LifeVest® wearable cardioverter defibrillator available from ZOLL Medical Corporation of Chelmsford, Mass. As shown, the wearable medical device 100 includes a harness 110 having a pair of shoulder straps and a belt that is worn about the torso of a patient. The harness 110 is typically made from a material, such as cotton, that is breathable, and unlikely to cause skin irritation, even when worn for prolonged periods of time. The wearable medical device 100 includes a plurality of ECG sensing electrodes 112 that are attached to the harness 110 at various positions about the patient's body and electrically coupled to a control unit 120 via a connection pod 130. The plurality of ECG sensing electrodes 112, which may be dry-sensing capacitance electrodes, are used by the control unit 120 to monitor the cardiac function of the patient and generally include a front/back pair of ECG sensing electrodes and a side/side pair of ECG sensing electrodes. Additional ECG sensing electrodes may be provided, and the plurality of ECG sensing electrodes 112 may be disposed at varying locations about the patient's body.

The wearable medical device 100 also includes a plurality of therapy electrodes 114 that are electrically coupled to the control unit 120 via the connection pod 130 and which are capable of delivering one or more therapeutic defibrillating shocks to the body of the patient, if it is determined that such treatment is warranted. As shown, the plurality of therapy electrodes 114 includes a first therapy electrode 114a that is disposed on the front of the patient's torso and a second therapy electrode 114b that is disposed on the back of the patient's torso. The second therapy electrode 114b includes a pair of therapy electrodes that are electrically coupled together and act as the second therapy electrode 114b. The use of two therapy electrodes 114a, 114b permits a biphasic shock to be delivered to the body of the patient, such that a first of the two therapy electrodes can deliver a first phase of the biphasic shock with the other therapy electrode acting as a return, and the other therapy electrode can deliver the second phase of the biphasic shock with the first therapy electrode acting as the return. The connection pod 130 electrically couples the plurality of ECG sensing electrodes 112 and the plurality of therapy electrodes 114 to the control unit 120, and may include electronic circuitry. For example, in one implementation the connection pod 130 includes signal acquisition circuitry, such as a plurality of differential amplifiers to receive ECG signals from different ones of the plurality of ECG sensing electrodes 112 and to provide a differential ECG signal to the control unit 120 based on the difference therebetween. The connection pod 130 may also include other electronic circuitry, such as a motion sensor or accelerometer by which patient activity may be monitored.

As shown in FIG. 1, the wearable medical device 100 also includes a user interface pod 140 that is electrically coupled to the control unit 120. The user interface pod 140 can be attached to the patient's clothing or to the harness 110, for example, via a clip (not shown) that is attached to a portion of the interface pod 140. Alternatively, the user interface pod 140 may simply be held in a person's hand. In some embodiments, the user interface pod 140 may communicate wirelessly with the control unit 120, for example, using a Bluetooth®, Wireless USB, ZigBee, Wireless Ethernet, GSM, or other type of communication interface. The user interface pod 140 typically includes a number a number of buttons by which the patient, or a bystander can communicate with the control unit 120, and a speaker by which the control unit 120 may communicate with the patient or the bystander. For example, where the control unit 120 determines that the patient is experiencing cardiac arrhythmia, the control unit 120 may issue an audible alarm via a loudspeaker (not shown) on the control unit 120 and/or the user interface pod 140 alerting the patient and any bystanders to the patient's medical condition. The control unit 120 may also instruct the patient to press and hold one or more buttons on the control unit 120 or on the user interface pod 140 to indicate that the patient is conscious, thereby instructing the control unit 120 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient. In some embodiments, the functionality of the user interface pod 140 may be integrated into the control unit 120.

The control unit 120 generally includes at least one processor, microprocessor, or controller, such as a processor commercially available from companies such as Texas Instruments, Intel, AMD, Sun, IBM, Motorola, Freescale and ARM Holdings. In one implementation, the at least one processor includes a power conserving processor arrangement that comprises a general purpose processor, such as an Intel® PXA270 processor and a special purpose processor, such as a Freescale™ DSP56311 Digital Signal Processor. Such a power conserving processor arrangement is described U.S. Pat. No. 8,904,214, titled SYSTEM AND METHOD FOR CONSERVING POWER IN A MEDICAL DEVICE, issued Dec. 2, 2014 which is incorporated by reference herein in its entirety. The at least one processor of the control unit 120 is configured to monitor the patient's medical condition, to perform medical data logging and storage, and to provide medical treatment to the patient in response to a detected medical condition, such as cardiac arrhythmia. Although not shown, the wearable medical device 100 may include additional sensors, other than the ECG sensing electrodes 112, capable of monitoring the physiological condition or activity of the patient. For example, sensors capable of measuring blood pressure, heart rate, thoracic impedance, pulse oxygen level, respiration rate, heart sounds, and the activity level of the patient may also be provided.

As discussed above, to provide protection against cardiac arrest, patients that use a wearable medical device, such as a wearable defibrillator, generally wear the device nearly continuously while they are awake and while they are asleep. Because the wearable medical device is worn nearly continuously, dry electrodes are typically used for both the plurality of ECG sensing electrodes 112 and the plurality of therapy electrodes 114 for comfort and to prevent irritation of the patient's skin. Where it is determined that one or more defibrillating shocks are to be delivered to the body of the patient and the patient is non-responsive, the control unit 120 sends a signal to the plurality of therapy electrodes 114 causing them to release an impedance reducing gel prior to delivery of one or more defibrillating shocks. The impedance reducing gel reduces the impedance between the conductive surface of the therapy electrodes and the patient's skin, thereby improving the efficiency of the energy delivered to the patient and reducing the chance of damage (e.g., in the form of burning, reddening, or other types of irritation) to the patient's skin.

Figure 2A:
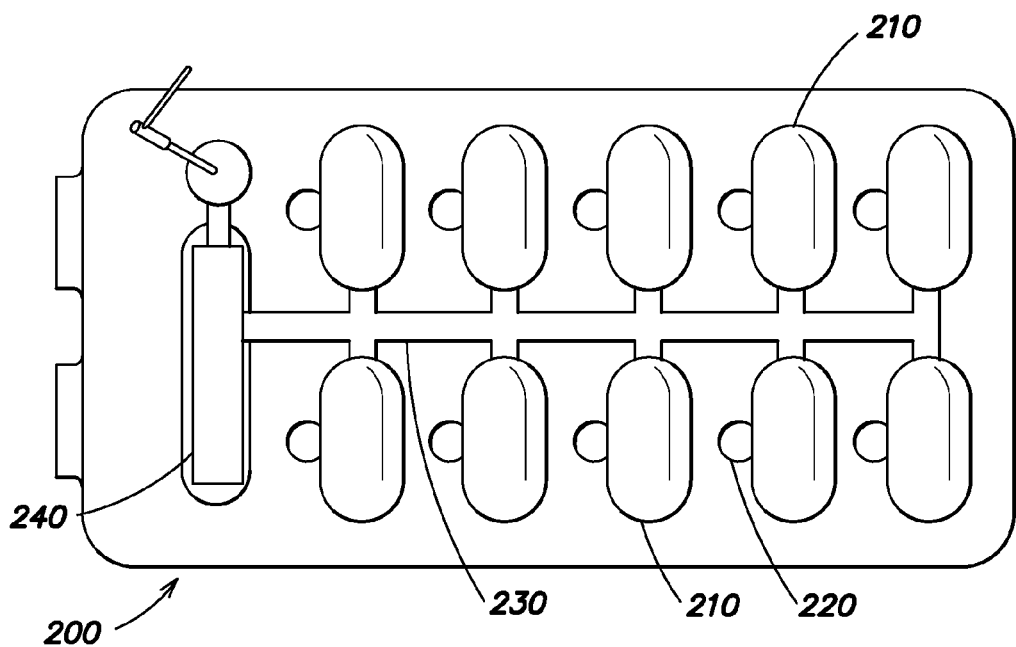
FIG. 2A is a top plan view of a therapy electrode assembly that may be used with the wearable medical device illustrated in FIG. 1.
Figure 2B:
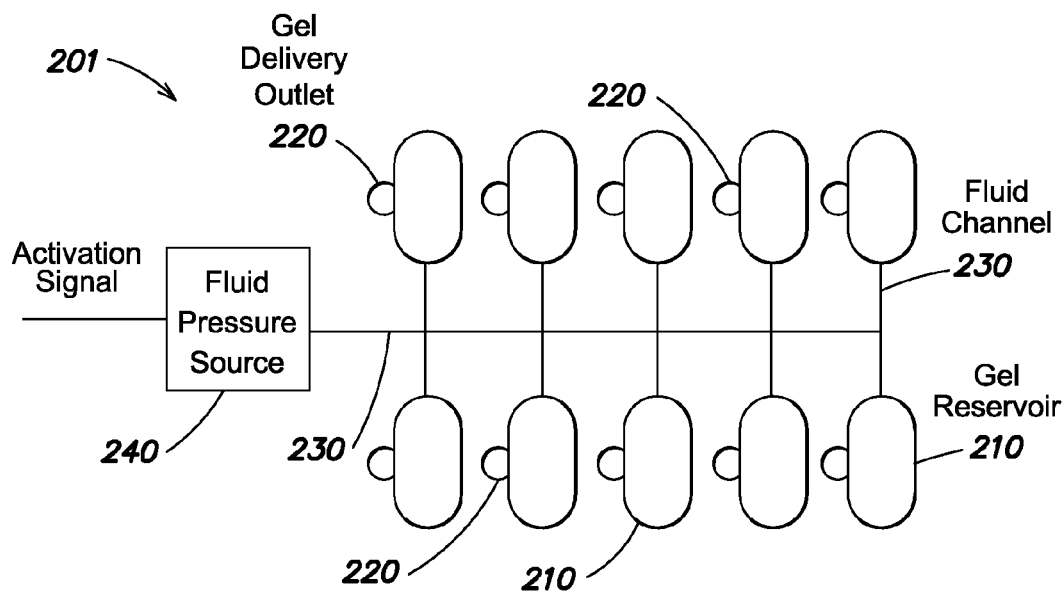
FIG. 2B is a functional block diagram of an impedance reduction system that may be included in the therapy electrode assembly of FIG. 2A.
Figure 2C:
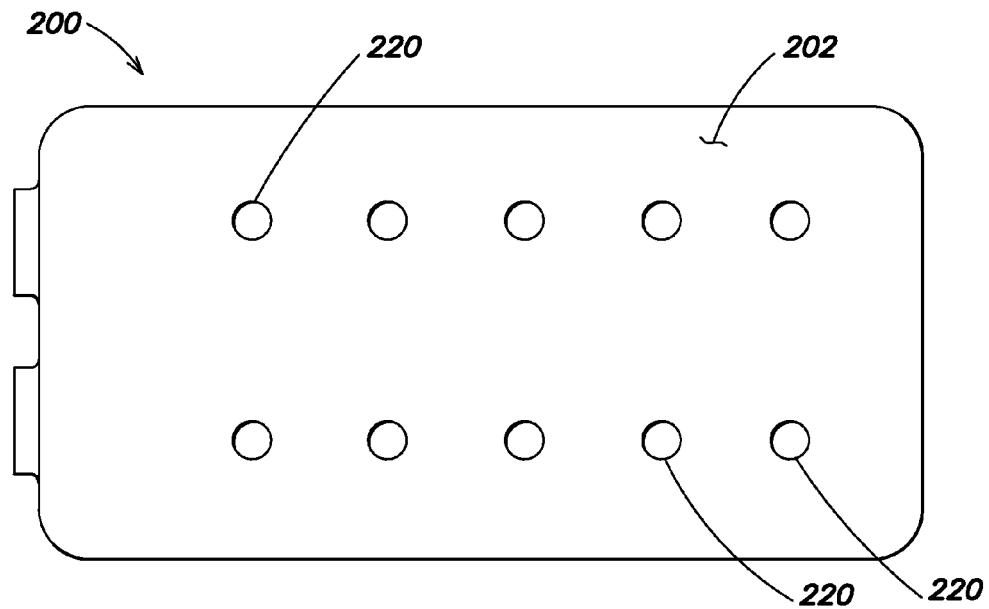
FIG. 2C is a bottom plan view of an electrode portion of the therapy electrode assembly of FIG. 2A.

FIG. 2A is a plan view of a therapy electrode assembly 200 that includes an impedance reduction system and which may be used with a wearable medical device, such as the wearable defibrillator described above with respect to FIG. 1. FIG. 2B is a functional block diagram of impedance reduction system 201 that is included in the therapy electrode assembly 200 shown in FIG. 2A. The impedance reduction system 201, when activated, dispenses an impedance reducing (i.e., electrically conductive) gel onto the exposed surface of the therapy electrode assembly that, in use, is placed most proximate to the patient's body. The therapy electrode assembly 200 is a multiple layer laminated structure that includes an electrically conductive layer disposed adjacent the bottom surface of the therapy electrode assembly 200 and an impedance reduction system 201. The electrically conductive layer forms the electrode portion 202 of the therapy electrode assembly 200 as shown in FIG. 2C. In use, the electrically conductive layer is disposed adjacent the patient's skin, although the conductive layer need not make direct contact with the patient. For example, portions of the harness 110 (FIG. 1) may be present between the electrically conductive layer and the patient's skin. As shown in FIG. 2A, the impedance reduction system 201 is disposed on a side of the therapy electrode assembly 200 (i.e., the top-side shown in FIG. 2A) that is opposite the side on which the conductive layer is formed.

The impedance reduction system 201 includes a plurality of conductive gel reservoirs 210, each of which has a respective gel delivery outlet 220, that are fluidly coupled to a fluid channel 230, and a fluid pressure source 240. The fluid pressure source 240 is fluidly coupled to the fluid channel 230, and when activated by an activation signal, forces a fluid, such as nitrogen gas, into the channel 230. The hydraulic pressure of the fluid from the activated fluid pressure source 240 in the fluid channel 230 forces the conductive gel stored in each of the plurality of gel reservoirs out of the plurality of gel delivery outlets 220 through apertures formed in the bottom surface of the electrode portion 202 and onto the exposed bottom surface of the electrode portion 202. The apertures are generally aligned with the plurality of gel delivery outlets 220 so that when activated, the electrically conductive gel is dispensed onto the exposed surface of the electrode portion that is disposed most proximate to the patient's body. Further details regarding the construction of the therapy electrode assembly 200 are described in U.S. Pat. No. 5,078,134 (hereinafter "the '134 patent") which is incorporated herein by reference in its entirety.

To perform effectively, it is desirable that the therapy electrode portion 202 be configured to conform to a variety of body contours and shapes so that in use, a significant, or in some embodiments, substantially an entire area of the bottom surface (the surface to be in contact with or positioned proximate a patient's body) of the electrode portion 202 is in intimate contact with a patient's body or with the fabric of a garment worn by the patient, for example, the wearable medical device 100 of FIG. 1. As a patient goes through daily routines including walking, sitting, sleeping, or performing other tasks, the patient's body shape and contours where a therapy electrode is positioned may be subject to various degrees of deformation. A therapy electrode may thus desirably be flexible and shape conforming to facilitate maintaining contact between a surface of the therapy electrode and a patient's body or garment.

Conventional therapy electrodes have traditionally been formed on a single non-segmented substrate which in some instances includes a flexible metal material or a polymeric material with a layer of metallic material deposited thereon.

FIGS. 3A-3E illustrate embodiments of a therapy electrode assembly 300 which may provide be more flexible and facilitate maintaining a greater amount of contact between a surface of the therapy electrode and a patient's body or garment than a conventional therapy electrode assembly. The substrate 305 of the electrode portion 302 of a therapy electrode assembly illustrated in FIGS. 3A-3E is divided into multiple connected segments 305a. The multiple segments 305a may move at least partially independently from one another. Each of the segments 305a may include at least one conductive gel reservoir 310 and at least one gel delivery outlet 320, which may be similar in construction and function as the gel reservoirs 210 and gel delivery outlets 220 described above. The various segments 305a may be at least partially physically separated from one another by, for example, one or more of a slot 315a, a gap 315b, or other open area between adjacent segments 305a. The various segments 305a may be physically coupled together by a central spine including one or more fluid conduits 330 configured to deliver fluid to the conductive gel reservoirs 310 to cause the release of conductive gel therefrom.

As illustrated, the slots 315a and/or gaps 315b may extend from a central portion of the substrate 305 of the therapy electrode assembly 300 proximate a central fluid conduit 330 and between adjacent segments 305a to an edge of the substrate 305. Providing for the various segments 305a of the electrode portion to move at least partially independently of one another may facilitate conformance of the electrode portion 302 to curves or contours of a patient's body. A segmented electrode portion 302 as illustrated in FIG. 3B may provide for a greater area, or a greater percentage of the total area, of the electrode portion to be in contact with the patient's body than if the electrode portion 302 were formed of a single, non-segmented substrate, such as illustrated in, for example, FIG. 2C.

In some embodiments, a segment 305b of a therapy electrode including a fluid pressure source 340 or other features, for example, an ECG electrode or a sensor for some other parameter indicative of a patient's medical condition may be at least partially physically separated from one or more of the segments 305a. This partial physical separation may be provided by including a slot 315a, a gap 315b, or other open area between a portion of the therapy electrode assembly 300 including the gel reservoirs 310 and the segment 305b of the therapy electrode assembly including the fluid pressure source 340 or other feature(s). In some embodiments, the segment 305b may be connected to the segments 305a by a fitting, for example, a tube 330a of a first diameter coupled to one of the segments 305a and 305b inserted into the bore of a tube 330b of a second diameter coupled to the other of the segments 305a and 305b, such as shown in FIG. 3C. Such a construction provides for the segment 305b to rotate relative to the segments 305a and may provide for a reduced tendency for the segment 305b of the electrode to constrain movement of the one or more segments 305a including the gel reservoirs 310.

Figure 3A:
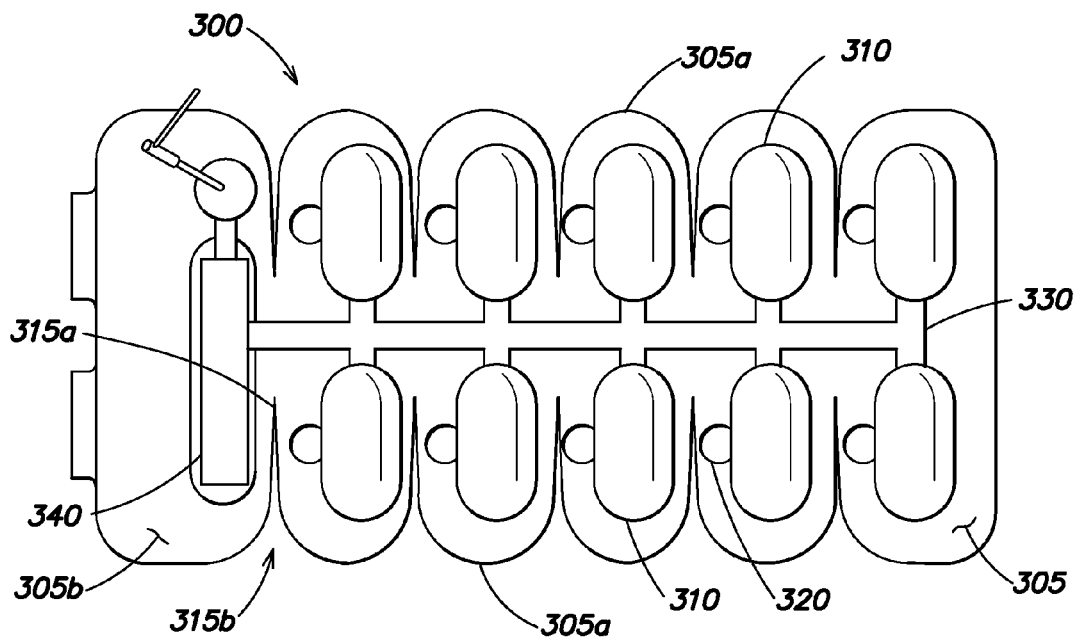
FIG. 3A is a top plan view of an electrode portion of a therapy electrode assembly that may be used with the wearable medical device illustrated in FIG. 1.
Figure 3B:
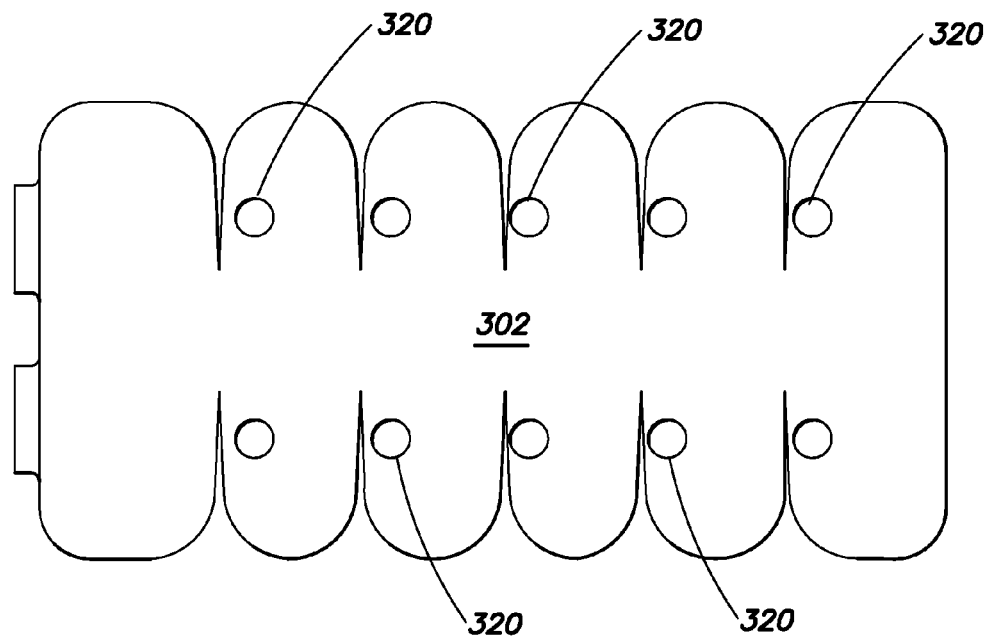
FIG. 3B is a bottom plan view of an electrode portion of a therapy electrode assembly that may be used with the wearable medical device illustrated in FIG. 1.
Figure 3C:
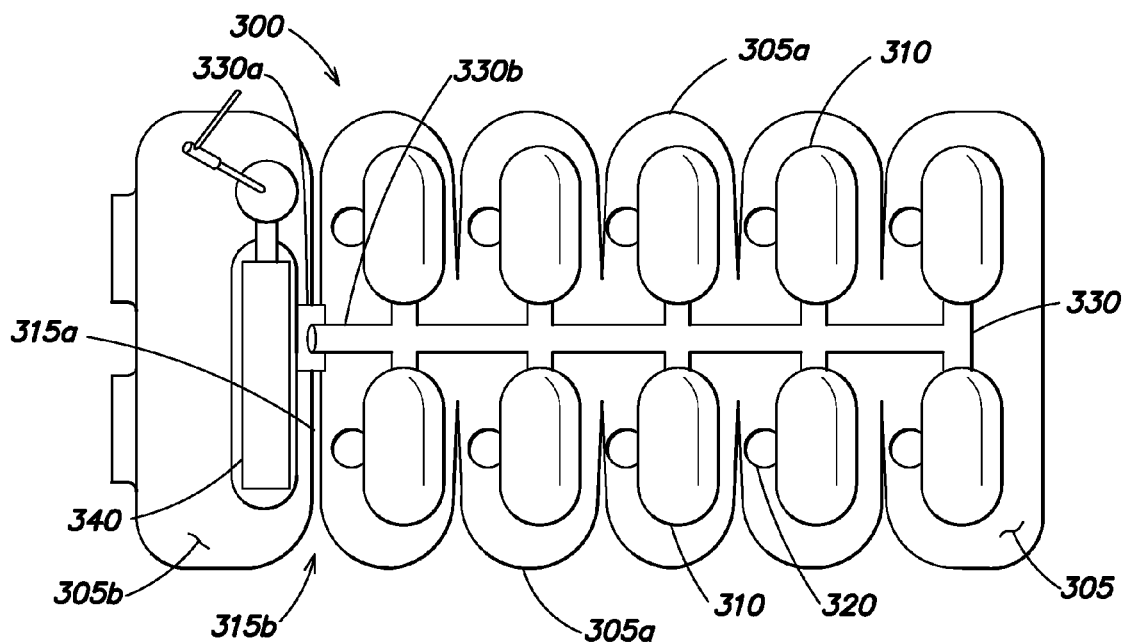
FIG. 3C is a top plan view of another electrode portion of a therapy electrode assembly that may be used with the wearable medical device illustrated in FIG. 1.
Figure 3D:
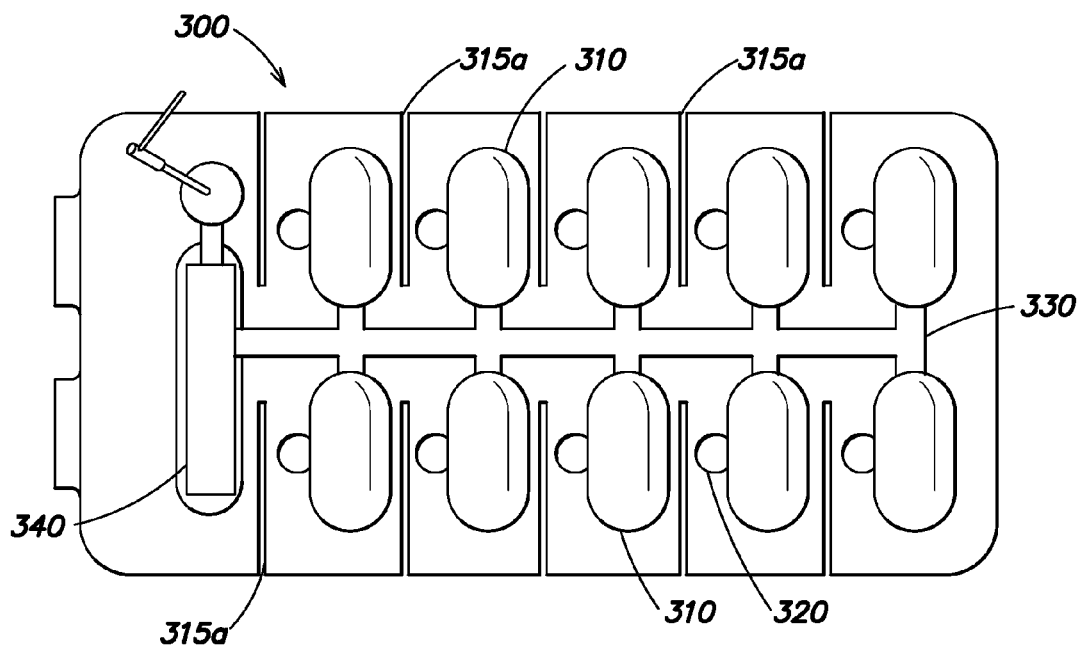
FIG. 3D is a top plan view of a therapy electrode assembly that may be used with the wearable medical device illustrated in FIG. 1.
Figure 3E:
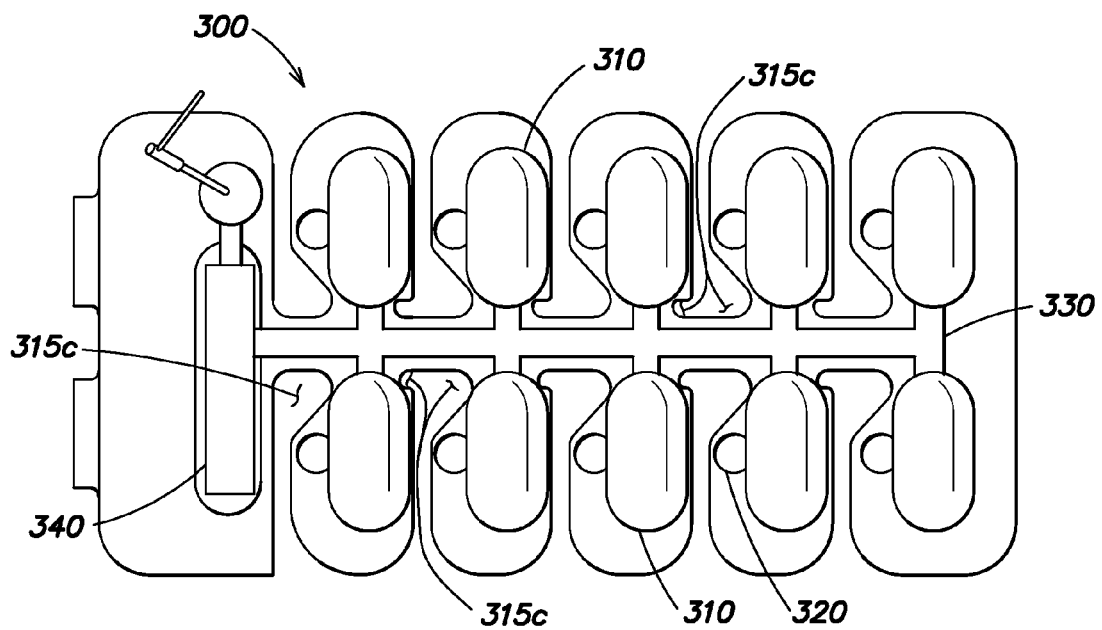
FIG. 3E is a top plan view of a therapy electrode assembly that may be used with the wearable medical device illustrated in FIG. 1.

As one of ordinary skill in the art would recognize, the shapes and positions of the segments 305a and 305b and of the slots 315a and/or gaps 315b may be provided in different configurations from those illustrated in FIG. 3A. For example, the various segments 305a may include rounded or squared ends or have different aspect ratios than illustrated. The slots 315a and/or gaps 315b may be curved as illustrated in FIG. 3A, squared as illustrated in FIG. 3D, or may include re-entrant portions 315c extending between one of the gel reservoirs 310 and gel delivery outlets 320 and a portion of the fluid conduit 330 as illustrated in FIG. 3E.

In some embodiments, the electrode portion 302 may include a metalized or otherwise conductive film on a portion of, or an entirety of, the bottom side of the electrode portion which is to be positioned against or face the skin of a patient. Prior to a defibrillating shock being delivered to the patient, conductive gel may be released from the gel reservoirs 310 to form a low impedance conductive path between the metalized side of the electrode portion 302 and the skin of the patient. Current may be applied through the metalized side of the electrode portion, the conductive gel, and the skin of the patient.

In other embodiments, the therapy electrode assembly 300 does not include a conductive film forming an electrode portion 302 on the bottom side of the electrode assembly 300 to be positioned against or face the skin of a patient. The majority of, or the entirety of the bottom surface of the electrode assembly 300 facing the skin of the patient may be substantially or completely non-conductive. Current may be applied to the patient to deliver a defibrillating shock by a method which does not involve passing current through or along any surface of the electrode assembly.

Figure 4:
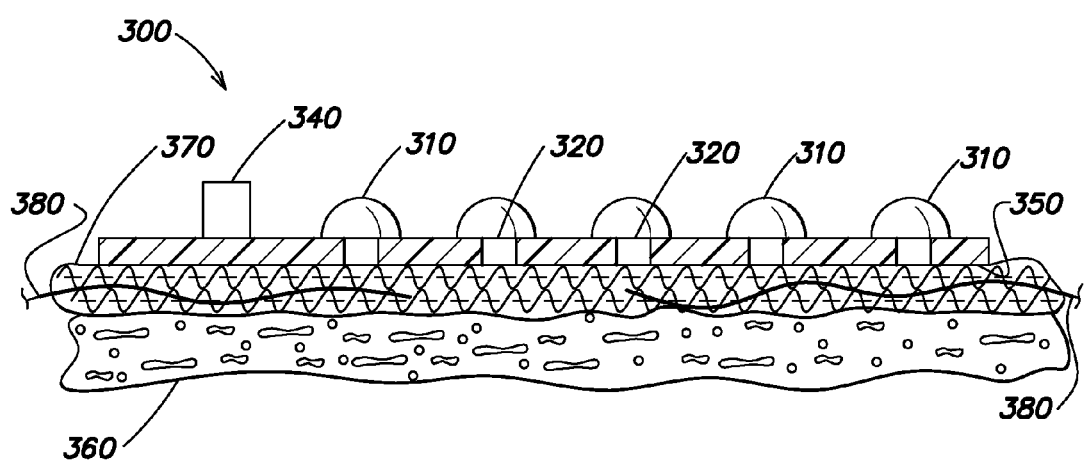
FIG. 4 is a cross sectional view of an electrode portion a therapy electrode assembly that may be used with the wearable medical device illustrated in FIG. 1 applied to fabric against the skin of a patient.

For example, as illustrated in FIG. 4, a therapy electrode assembly 300 having no conductive material present on the surface 350 facing the skin 360 of a patient may be disposed in a pocket in a garment worn by the patient or otherwise secured to an external surface of the garment. As used herein, the term "garment" includes clothing, for example, a shirt or jacket, as well as wearable medical devices, for example, a LifeVest® wearable cardioverter defibrillator.

The substrate 305 of the therapy electrode assembly 300 may be formed of a natural or synthetic fabric, for example, cotton, wool, or polyester. In instances where the substrate is not waterproof, the gel reservoirs 210, 310 may be formed with a membrane, for example, a plastic film, where the gel reservoirs contact the fabric to facilitate retaining conductive gel within the gel reservoirs and prevent it from escaping through the substrate. In other embodiments, the fabric may include a waterproof coating where the gel reservoirs 210, 310 contact the fabric. Forming the substrate 305 out of a fabric material may provide for the substrate to easily conform to the contours of the body of a patient. The substrate 305 may include perforations. Forming the substrate 305 out of a fabric material and/or with perforations may facilitate passage of conductive gel through the substrate upon release of the conductive gel from the gel reservoirs 210, 310.

Fabric 370 of the garment between the surface 350 of the therapy electrode assembly 300 and the skin 360 of the patient may be conductive and/or may include conductive stitching 380. Upon release of conductive gel from the gel reservoirs 310 through the gel delivery outlets 320, the conductive gel may pass through the weave of the fabric 370 and may contact the conductive stitching 380 and the skin 360 of the patient on the opposite side of the garment fabric 370 from the surface 350. The released conductive gel may form a low impedance conductive path between the conductive stitching 380 or conductive fabric of the garment and the skin 360 of the patient. A defibrillating shock may be delivered to the patient through the conductive stitching 380 or conductive fabric of the garment and through the released conductive gel into the skin of the patient.

The therapy electrode assembly 300 may be provided with a relatively large, easy-to-grip pull tab 495 (illustrated in FIG. 5) to facilitate insertion or removal of the therapy electrode assembly 300 from a pocket of a garment or wearable medical device. In accordance with one embodiment, the pull tab 495, or another visible surface of the therapy electrode assembly may include an indicator that identifies whether the impedance resistance system has been activated or not. Such indicators may include, for example, an additional gel reservoir coupled to the fluid channel which may release a dye or other colored substance upon activation of the impedance reduction system. The indicator may also include, for example, a section of wiring, or a fuse or other device which may change color responsive to the application of electrical energy to the electrode. Other indicator devices known to those in the art are also contemplated and embodiments of the present invention are not limited to any particular indicator device.

Figure 5:
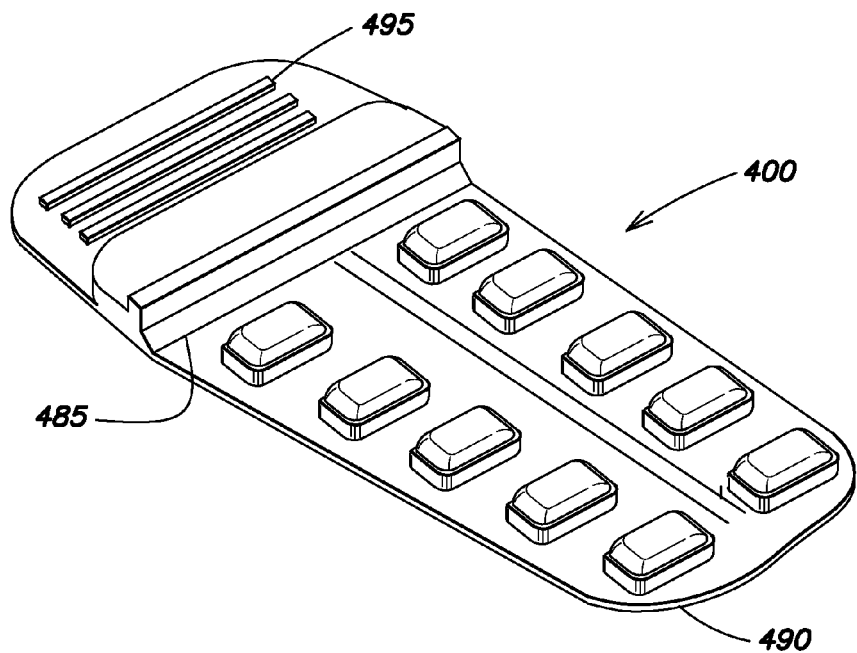
FIG. 5 is an elevational view of a therapy electrode assembly that may be used with the wearable medical device illustrated in FIG. 1.
Figure 6A:
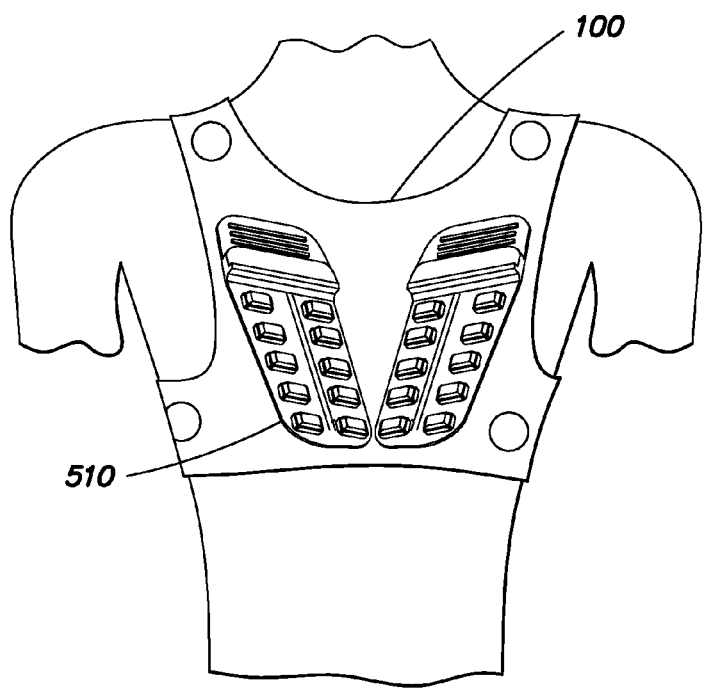
FIG. 6A illustrates placement of therapy electrode assemblies in a rear portion of a wearable medical device.
Figure 6B:
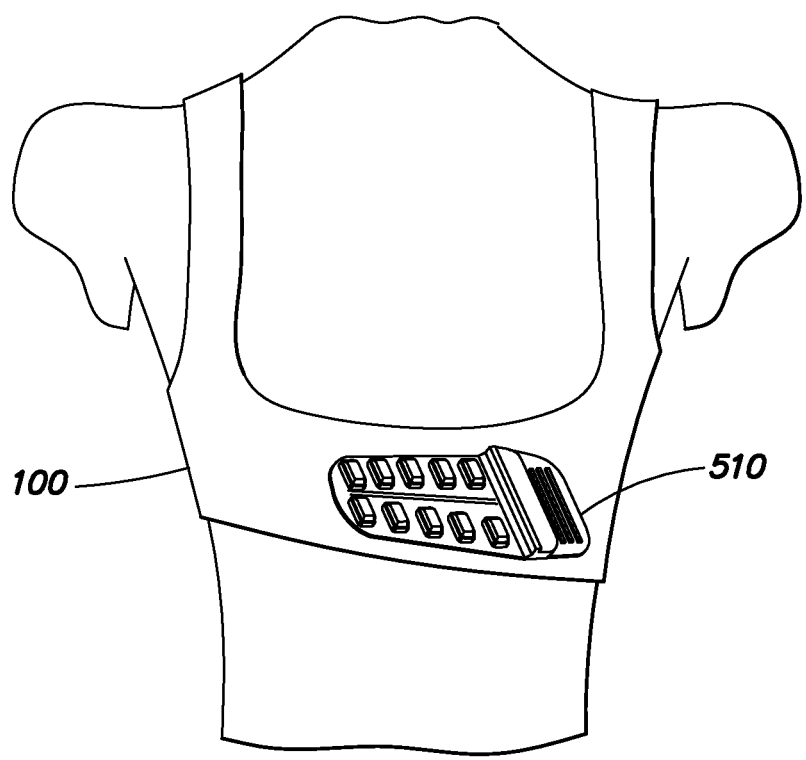
FIG. 6B illustrates placement of a therapy electrode assembly in a front portion of a wearable medical device.
Figure 6C:
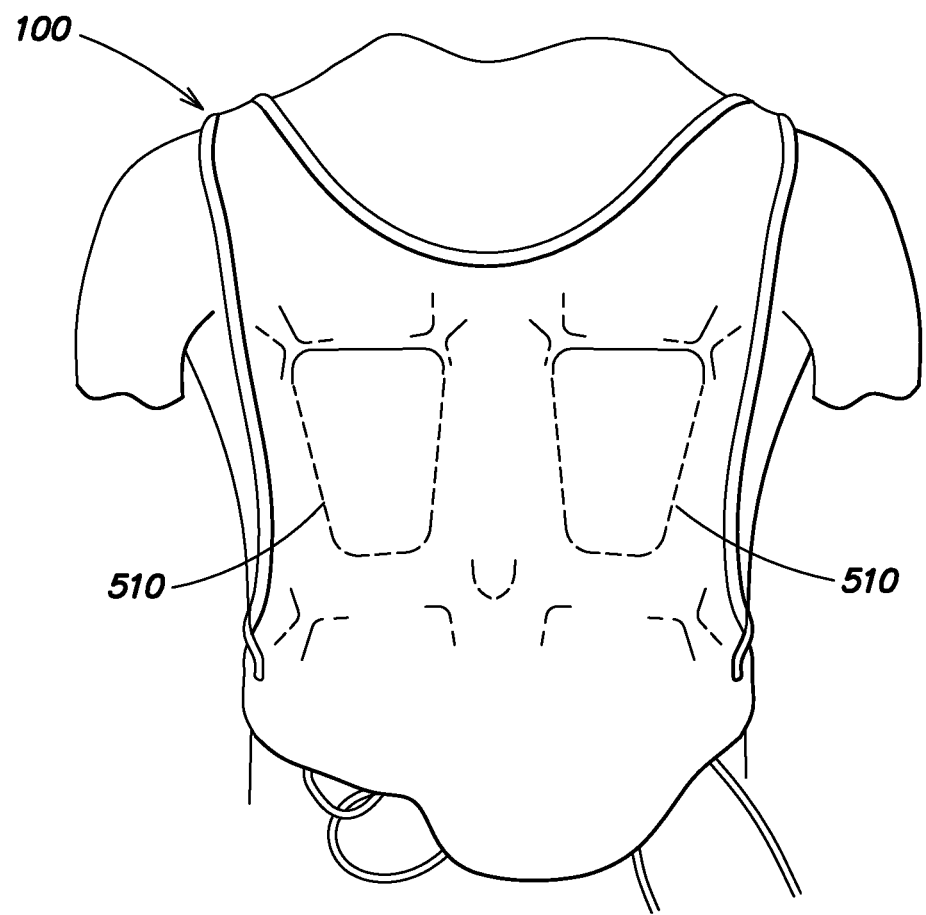
FIG. 6C is a plan view of the rear of a wearable medical device including tapered pockets for therapy electrode assemblies.

Therapy electrode assemblies in accordance with various embodiments may include one or more features which facilitate proper insertion of the therapy electrode assembly into a garment to be worn by a patient. For example, as illustrated in FIG. 5, a therapy electrode assembly 400 may be formed with a tapered shape. A first end 485 of the therapy electrode assembly 400, for example, an end proximate the fluid pressure source (not visible in FIG. 5), when present, may be wider than a second end 490 of the therapy electrode assembly 400, for example, an end distal from the fluid pressure source. The provision of corresponding tapered pockets 510 on a wearable medical device 100 as illustrated in FIGS. 6A and 6B (where the fabric overlying the therapy electrode assemblies is removed for clarity) allows therapy electrode assemblies 400 to be inserted only tapered end first. FIG. 6C illustrates a rear side of a wearable medical device 100 including tapered pockets 510 in which tapered therapy electrode assemblies may be placed and which may limit the direction in which the tapered therapy electrode assemblies are inserted.

The shape of tapered therapy electrode assemblies 400 are not limited to that illustrated in the figures. In some embodiments, both edges of a therapy electrode assembly 400 may be tapered and in other embodiments only a single edge is tapered. The degree of taper on each edge of a therapy electrode assembly 400 may differ. In some embodiments, a portion of one or both edges of a therapy electrode assembly 400 may include a cut out portion, which may be, for example, rectangular, instead of a gradually tapering profile as illustrated. A therapy electrode assembly 400 in accordance with embodiments of the present invention may be shaped in any manner which may facilitate insertion of the therapy electrode into the pocket in a correct orientation.

Figure 7:
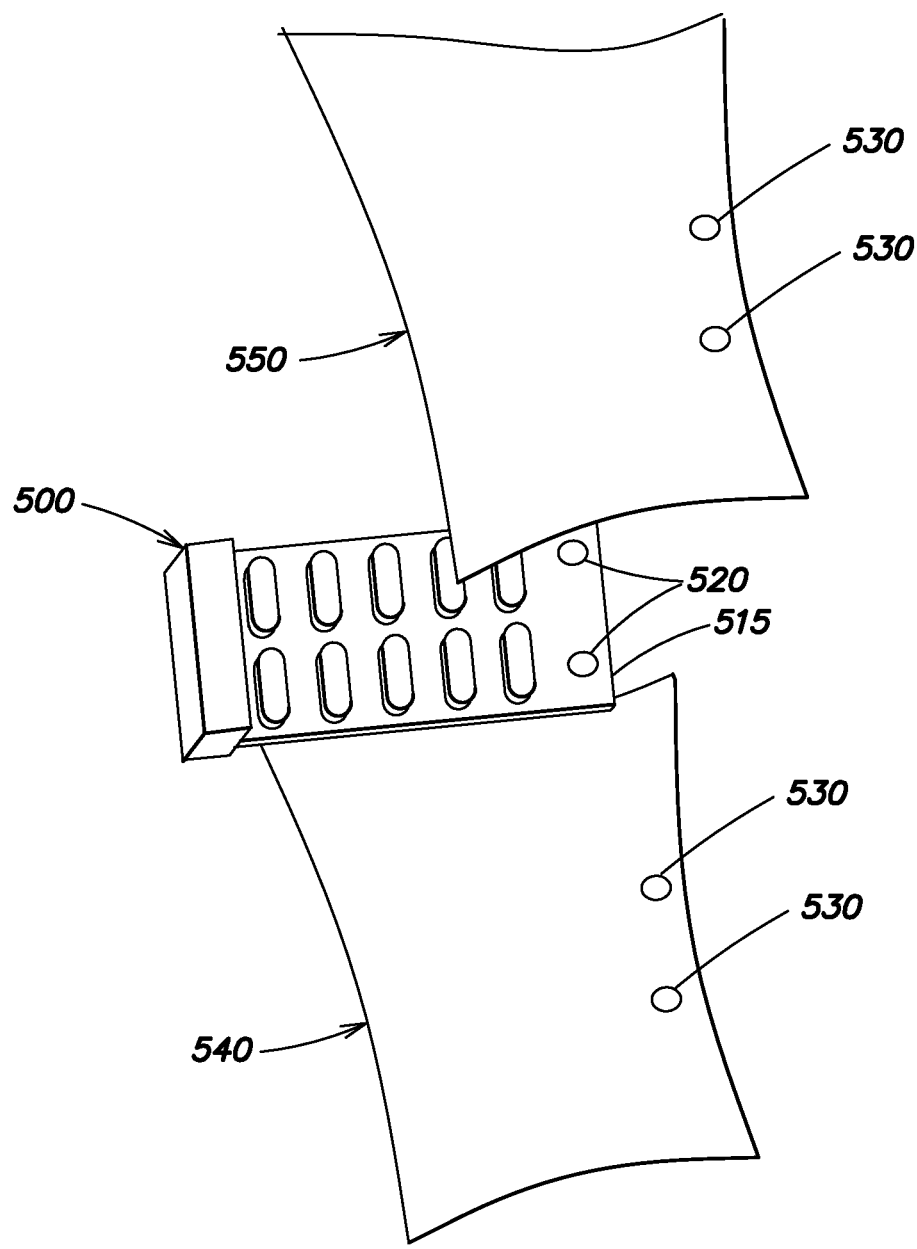
FIG. 7 is an exploded view of a pocket of a wearable medical device and therapy electrode assembly intended to reside within the pocket.

An additional feature which may facilitate proper insertion of the therapy electrode assembly into a garment to be worn by a patient is illustrated in FIG. 7, which is an exploded view of portions of a pocket of a garment and a therapy electrode assembly 500 intended to be placed within the pocket. The therapy electrode assembly 500 of FIG. 7 includes two magnets 520 located on the substrate 515. Corresponding magnets 530 may be located on material forming inner and/or outer portions 540, 550, respectively, or both, of a pocket of a wearable medical device 100 into which the therapy electrode assembly 500 is to be inserted. The magnets 520, 530 may be arranged such that the magnets 530 in the material of the pocket will be repelled from the magnets 520 in the substrate unless the therapy electrode assembly 500 is inserted properly, for example, with the side onto which the conductive gel is to be released facing the side of the pocket against the skin of a patient. For example, each of the magnets 520 could be arranged with North poles facing in a direction away from an electrode side of the therapy electrode assembly 500 and South poles facing in an intended direction of the body of a patient wearing the wearable medical device 100. The fabric of the outer portion of the pocket could then include magnets with North poles facing inward toward the side of the garment intended to lie against the skin of the patient. The fabric of the inner portion of the pocket could include magnets with South poles facing away from the side of the garment intended to lie against the skin of the patient. Unless the magnets were attracted to each other and "clicked" together, a patient would know that the therapy electrode assembly 500 was not properly inserted into the pocket. Fewer or greater than two magnets may be included in any of the therapy electrode assembly 500 and either one or both of the inner and outer portions 540, 550, respectively, of the pocket of the wearable medical device 100. The orientation of the poles of the magnets could be altered as desired.

In alternate embodiments, one or more of the magnets 520, 530 may be replaced or supplemented by snaps having male sides and female sides. For example, a female side of a snap may be placed on the surface of the upper side (the side intended to face away from a patient) of the substrate. A corresponding male half of the snap may be provided on the internal surface of fabric of an outer layer of a pocket of a wearable medical device 100 into which the therapy electrode assembly 500 is intended to be inserted. The male and female portions of the snap would only be able to engage if the therapy electrode assembly 500 was inserted into the pocket in the correct orientation. Other directional snaps or fasteners having male and female sides, for example, hook and loop fasteners, may also or alternatively be used.

Applicants have appreciated that there may be instances where it would be desirable to have redundancy in the impedance reduction system described above. An electrode that incorporates redundant impedance reduction systems is now described with respect to FIGS. 8-10 below.

Figure 8:
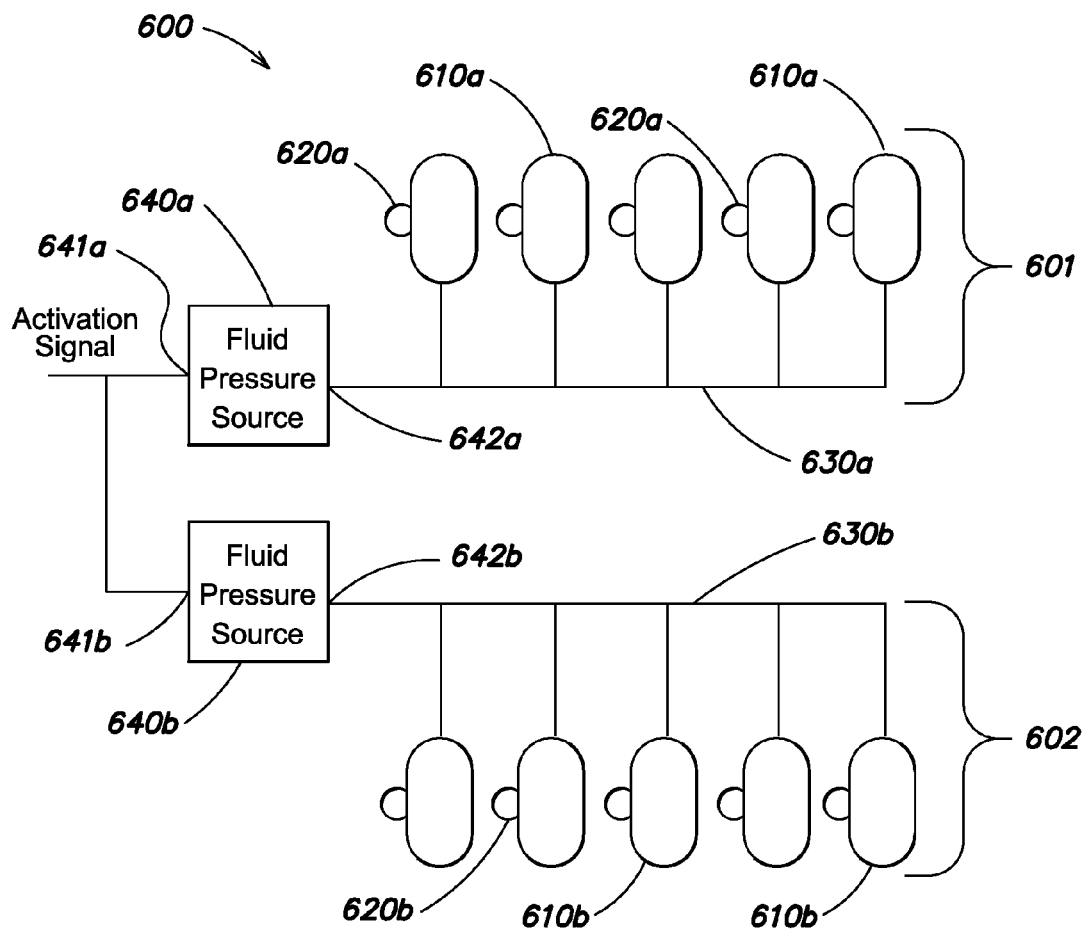
FIG. 8 is a functional block diagram of a redundant impedance reduction system in accordance with an aspect of the present invention.

FIG. 8 is a functional block diagram of a redundant impedance reduction system that may be incorporated into a therapy electrode assembly in accordance with an aspect of the present invention. As shown, the redundant impedance reduction system 600 includes at least two independent impedance reduction systems 601, 602 similar in construction and operation to that described previously with respect to FIGS. 3A-3E. Although only two impedance reduction systems 601, 602 are shown in FIG. 8, it should be appreciated that additional impedance reduction systems may be provided.

As shown, a first impedance reduction system 601 of the at least two impedance reduction systems 601, 602 includes a first plurality of gel reservoirs 610a, each containing an electrically conductive gel, with each respective gel reservoir including a gel delivery outlet 620a. Each of the first plurality of gel reservoirs 610a is fluidly coupled to a first fluid channel 630a that is, in turn, fluidly coupled to a first fluid pressure source 640a. The first fluid pressure source 640a has an input 641a to receive a first electrical activation signal and a fluid outlet 642a that is fluidly coupled to the first fluid channel 630a. A rupturable membrane and/or a filter (not shown) may be positioned between the fluid outlet 642a and the first fluid channel 630a as described in the '134 patent. As described in the '134 patent, the first fluid pressure source 640a may include a gas generating cartridge that ignites a chemical pellet (such as a lead styphnate igniter and a gas generating mixture of ammonium dichromate and nitroguanidine) that rapidly decomposes and generates quantities of a gas, such as nitrogen. It should be appreciated that other types of fluid pressure sources may be used, as the present invention is not limited to any particular type of fluid pressure source.

In response to the first activation signal received at the input 641a of the first fluid pressure source 640a, a fluid, such as nitrogen gas, is forced into the first fluid channel 630a and then into each of the first plurality of gel reservoirs 610a. The hydraulic pressure of the fluid flowing into each of the first plurality of gel reservoirs 610a forces the electrically conductive gel contained in each gel reservoir toward its respective gel delivery outlet 620a, thereby fracturing a membrane separating the gel delivery outlet from a respective aperture formed in the electrically conductive layer of the electrode portion.

The second impedance reduction system 602 of the at least two impedance reduction systems 601, 602 is similar to the first impedance reduction system 601 and includes a second plurality of gel reservoirs 610b, each containing an electrically conductive gel, with each respective gel reservoir including a gel delivery outlet 620b. The electrically conductive gel contained in the second plurality of gel reservoirs 610b may, but need not, be the same type of gel as that contained in the first plurality of gel reservoirs 610a. For example, the electrically conductive gel contained in the second plurality of gel reservoirs 610b may have a different color, or have a longer drying time than the gel contained in the first plurality of gel reservoirs 610a. Each of the plurality of gel reservoirs 610b is fluidly coupled to a second fluid channel 630b that is, in turn, fluidly coupled to a second fluid pressure source 640b. The second fluid pressure source 640b has an input 641b to receive a second electrical activation signal and a fluid outlet 642b that is fluidly coupled to the second fluid channel 630b. The second fluid pressure source 640b may similar in construction to the first fluid source 640a described above.

As shown in FIG. 8, the input 641a of the first fluid pressure source 640a may be electrically connected to the input 641b of the second fluid pressure source, such that a single activation signal activates each of the at least two impedance reduction systems 601, 602 substantially simultaneously. Should one of the redundant impedance reduction systems 601, 602 fail to operate (either partially or completely), the other can still operate to dispense conductive gel onto the exposed surface of the electrode. The activation signal provided to the input 641a of the first fluid pressure source 640a may be provided by the control unit 120 (FIG. 1) to the first fluid pressure source 640a using an electrical conductor that is physically distinct from that which provides the activation signal to the input 641b of the second fluid pressure source 640b to permit further redundancy, for example, should one of the electrical conductors be damaged. Alternatively, a single electrical conductor may be provided between the control unit 120 and the electrode assembly, with the single electrical conductor being connected to both the input 641a of the first fluid pressure source 640a and the input 641b of the second fluid pressure source 640b.

It should be appreciated that each of the first and second pressure sources 640a, 640b may alternatively receive separate activation signals, as the present invention is not limited to receiving a single activation signal. The separate activation signals may be sent, for example by the control unit 120, to each of the first fluid pressure source 640a and the second fluid pressure source 640b at substantially the same time, or at different times. For example, a first activation signal may be provided to the input 641a of the first fluid pressure source 640a at a first time, and a second activation signal may be provided to the input 641b of the second fluid pressure source 640b at a second time that is subsequent to the first time. In accordance with one embodiment, the control unit 120 (FIG. 1) may send the first activation signal to the first fluid pressure source 640a at a first time, and send the second activation signal to the second fluid pressure source 640b at a second and subsequent time where it is determined that the first impedance reduction system 601 failed to operate. Alternatively, the second activation signal may be sent to the second fluid pressure source 640b at a second and subsequent time even where activation of the first fluid pressure source 640a is successful. Such a subsequent activation of the second fluid pressure source 640b would permit a second deployment of conductive gel onto the exposed surface of the electrode and permit the electrode to maintain a high conductivity with the patient for a longer period of time than if both impedance reduction systems 601, 602 were activated at substantially the same time.

Figure 9:
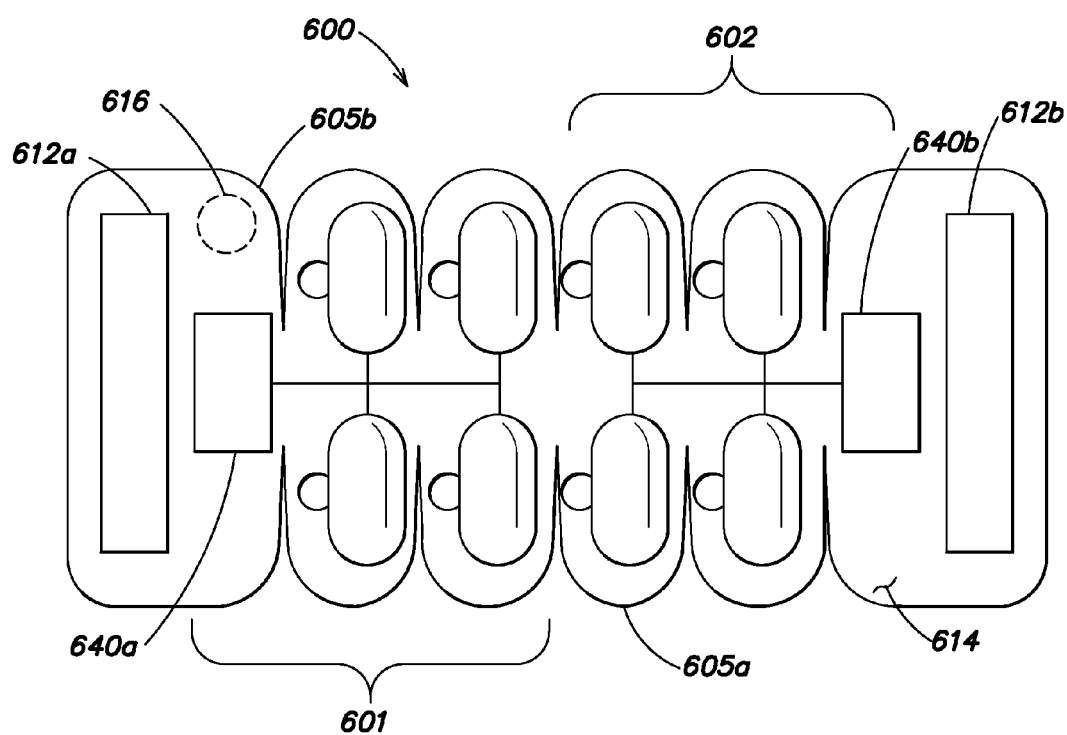
FIG. 9 is a schematic diagram of an electrode assembly that includes ECG sensing electrodes, a therapy electrode, and redundant impedance reduction systems in accordance with another aspect of the present invention.

FIG. 9 illustrates a therapy electrode assembly that combines one or more ECG sensing electrodes, a therapy electrode, and redundant impedance reduction systems in a single integrated electrode assembly in accordance with a further aspect of the present invention. As shown, the electrode assembly 600 includes a pair of ECG sensing electrodes 612a, 612b for monitoring the cardiac function of a patient. The electrode assembly 600 further includes a therapy electrode 614, and at least two impedance reduction systems 601, 602, similar to those described previously with respect to FIG. 8. It should be appreciated that in an alternative embodiment, only a single impedance reduction system may be provided. The pair of ECG sensing electrodes 612a, 612b may be electrically separated from the therapy electrode 614, for example, by an insulator. It should be appreciated that in other embodiments, the electrode assembly 600 may include only a single ECG sensing electrode, while in other embodiments, more than two ECG sensing electrodes may be provided. In such alternative embodiments, the number and placement of ECG sensing electrodes and may vary from that shown in FIG. 9. The electrode assembly 600 may include one or more sections 605a which may include one or more gel reservoirs and/or fluid channels, and which may be at least partially separated from one or more other sections 605a and/or sections 605b which may include the sensing electrodes 612a, 612b and/or pressure sources 640a, 640b. The one or more sections 605a, 605b may be at least partially physically separated from one another by slots and/or gaps as described above with reference to FIGS. 3A-3D.

In yet a further embodiment, the integrated electrode assembly can include additional sensors 616, other than the one or more ECG sensing electrodes and the therapy electrode, that are capable of monitoring other physiological parameters of a patient, such as blood pressure, heart rate, thoracic impedance, pulse oxygen level, respiration rate, heart sounds, etc.

Figure 10:
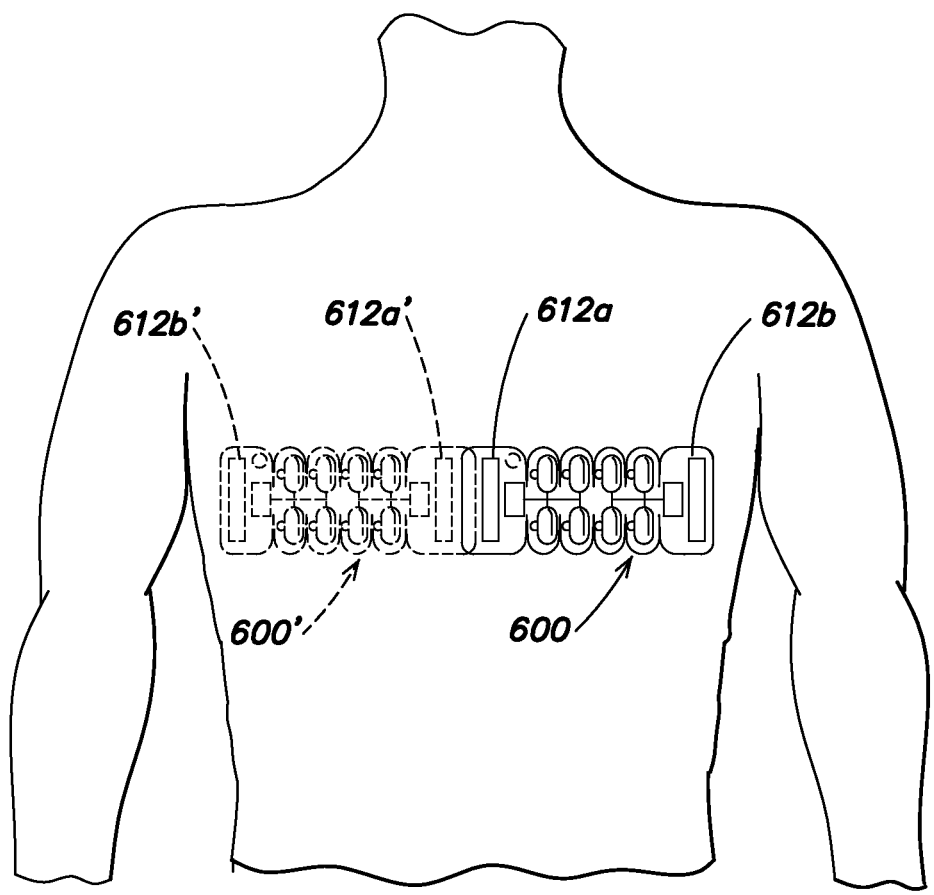
FIG. 10 illustrates a manner in which the electrode assembly of FIG. 9 may be worn on the body of a patient.

The electrode assembly 600 may be worn on the patient's body such that one of the pair of ECG sensing electrodes 612a, 612b is disposed approximately in the center of the patient's torso, and the other of the pair of ECG sensing electrodes 612a, 612b is disposed on the side of the patient's torso. For example, as shown in FIG. 10, the electrode assembly 600 may be worn on the front of the patient's torso, so that the ECG sensing electrode 612a is disposed approximately in the center of the patient's chest, and the other ECG sensing electrode 612b is disposed on the patient's side. A second electrode assembly 600' may be worn on the back of the patient's torso to provide a second pair of ECG sensing electrodes 612a', 612b', so that one of the ECG sensing electrodes (e.g., ECG sensing electrode 612a') of the second pair of ECG sensing electrodes 600' is disposed approximately in the center of the patient's back, and the other ECG sensing electrode (e.g., ECG sensing electrode 612b') of the second pair of ECG sensing electrodes 600' is disposed on the patient's side opposite the other ECG sensing electrode (e.g., ECG sensing electrode 612b) of the first pair of ECG sensing electrodes 612a, 612b, as shown in FIG. 10. Such an arrangement provides a front-to-back pairing of ECG sensing electrodes (e.g., 612a, 612a') and a side-to-side pairing of ECG sensing electrodes (e.g., 612b, 612b'). It should be appreciated that other placements for the first electrode assembly 600 and the second electrode assembly 600' may alternatively be used. For example, the first electrode assembly 600 may be placed on one side of the patient's torso, and the second electrode assembly 600' placed on the other side of the patient's torso to provide side-to-side pairings of ECG sensing electrodes.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A therapy electrode system comprising:
a garment wearable on a torso of a patient;
a pocket formed in the garment; and
a therapy electrode configured to be inserted into the pocket, at least one of the pocket and the therapy electrode including a feature discouraging insertion of the therapy electrode into the pocket in an incorrect orientation, wherein the feature comprises the pocket being tapered from a first pocket end to a second pocket end and the therapy electrode being tapered from a first therapy electrode end to a second therapy electrode end.

2. The therapy electrode system of claim 1, wherein the feature further comprises a shape of the pocket which conforms to a shape of the therapy electrode.

3. The therapy electrode system of claim 1, wherein both a first edge of the therapy electrode is tapered and a second edge of the therapy electrode, opposite the first edge, is tapered.

4. The therapy electrode system of claim 3, wherein the first edge of the therapy electrode is tapered to a different degree than the second edge of the therapy electrode.

5. The therapy electrode system of claim 1, wherein a first edge of the therapy electrode is tapered and a second edge of the therapy electrode, opposite the first edge, is not tapered.

6. The therapy electrode system of claim 1, wherein one edge of the therapy electrode includes a cut out portion.

7. The therapy electrode system of claim 1, wherein the feature further comprises a first magnet disposed on the therapy electrode and a second magnet disposed on the garment.

8. The therapy electrode system of claim 7, wherein the second magnet is disposed on material forming the pocket.

9. The therapy electrode system of claim 1, wherein the feature further comprises a fastener including a male side disposed on one of the therapy electrode and the garment and a female side disposed on the other one of the therapy electrode and the garment.

10. The therapy electrode system of claim 9, wherein the feature further comprises a first snap portion disposed on the therapy electrode and a second snap portion disposed on the garment.

11. The therapy electrode system of claim 9, wherein the feature further comprises hook and loop fasteners.

12. The therapy electrode system of claim 1, wherein the therapy electrode includes a pull tab configured to facilitate insertion and/or removal of the therapy electrode from the pocket.

13. A therapy electrode system comprising:
a garment wearable on a torso of a patient;
a pocket formed in the garment; and
a therapy electrode configured to be inserted into the pocket, the pocket tapered from a first pocket end to a second pocket end, the therapy electrode tapered from a first therapy electrode end to a second therapy electrode end, a taper of the pocket and a taper of the therapy electrode discouraging insertion of the therapy electrode into the pocket in an incorrect orientation.

14. The therapy electrode system of claim 13, further comprising
a closing mechanism including a first portion disposed on the therapy electrode and a second portion disposed on the garment, the closing mechanism discouraging insertion of the therapy electrode into the pocket in an incorrect orientation.

15. The therapy electrode system of claim 14, wherein the first portion includes a first magnet and the second portion includes a second magnet.

16. The therapy electrode system of claim 14, wherein the closing mechanism includes a male side of a fastener disposed on one of the therapy electrode and the garment and a female side of the fastener disposed on the other one of the therapy electrode and the garment.

17. The therapy electrode system of claim 14, wherein the closing mechanism includes a first snap portion disposed on the therapy electrode and a second snap portion disposed on the garment.

18. The therapy electrode system of claim 14, wherein the closing mechanism includes hook and loop fasteners.

19. A therapy electrode system comprising:
a garment wearable on a torso of a patient;
a pocket formed in the garment; and
a therapy electrode configured to be inserted into the pocket, at least one of the pocket and the therapy electrode including a feature discouraging insertion of the therapy electrode into the pocket in an incorrect orientation, wherein one edge of the therapy electrode includes a cut out portion.

* * * * *